(12) United States Patent
Griffis et al.

(10) Patent No.: US 6,949,104 B2
(45) Date of Patent: Sep. 27, 2005

(54) GUIDE WIRE STEERING HANDLE

(76) Inventors: Jack Griffis, 1133 Druid Lake, Decatur, GA (US) 30033; Paul Gianneschi, 1415 Woodland Lake Dr., Snellville, GA (US) 30078

( * ) Notice: Subject to any disclaimer, the term of this patent is extended or adjusted under 35 U.S.C. 154(b) by 554 days.

(21) Appl. No.: 10/157,959

(22) Filed: May 31, 2002

(65) Prior Publication Data

US 2003/0225395 A1 Dec. 4, 2003

(51) Int. Cl.$^7$ ................................................ A61F 11/00
(52) U.S. Cl. ........................................ 606/108; 600/434
(58) Field of Search ............................... 600/434, 585; 604/159, 95.01, 171, 528; 606/198, 194, 191, 103, 108; 24/535–537, 132 WL

(56) References Cited

U.S. PATENT DOCUMENTS

| | | | |
|---|---|---|---|
| 3,312,128 A | | 4/1967 | Wasson |
| 4,860,742 A | | 8/1989 | Park et al. |
| 4,957,117 A | * | 9/1990 | Wysham ..................... 600/585 |
| 4,973,329 A | | 11/1990 | Park et al. ..................... 606/1 |
| 5,137,288 A | * | 8/1992 | Starkey et al. ................. 279/42 |
| 5,161,534 A | | 11/1992 | Berthiaume ................. 128/657 |
| 5,312,338 A | | 5/1994 | Nelson et al. ................. 604/95 |
| 5,325,746 A | | 7/1994 | Anderson ..................... 81/487 |
| 5,325,868 A | | 7/1994 | Kimmelstiel ................. 128/772 |
| 5,392,778 A | * | 2/1995 | Horzewski ................... 600/434 |
| 5,423,331 A | | 6/1995 | Wysham ..................... 128/772 |
| 5,634,475 A | | 6/1997 | Wolvek ....................... 128/772 |
| 5,851,189 A | * | 12/1998 | Forber .......................... 600/585 |
| 6,030,349 A | | 2/2000 | Wilson et al. ............... 600/585 |
| 6,033,414 A | * | 3/2000 | Tockman et al. ........... 606/129 |
| 6,059,484 A | * | 5/2000 | Greive ........................ 403/305 |
| 6,485,466 B2 | * | 11/2002 | Hamilton ..................... 604/158 |
| 6,533,772 B1 | | 3/2003 | Sherts et al. |

* cited by examiner

*Primary Examiner*—Julian W. Woo
*Assistant Examiner*—Victor Nguyen
(74) *Attorney, Agent, or Firm*—Welsh & Flaxman LLC

(57) ABSTRACT

A guidewire steering device includes a gripping member and a compression member. The gripping member includes opposed first and second gripping surfaces positioned for selective engagement of a guidewire positioned therebetween. The first gripping surface includes a first end and a second end and the second gripping surface includes a first end and a second end. The first and second gripping surfaces being oriented to permit selective gripping of a guidewire positioned therebetween. The second end of the first gripping surface and the second end of the second gripping surface are spaced apart in a manner defining a lateral access slot through which a guidewire may be passed for positioning between the first and second gripping surfaces. The compression member is positioned about the gripping member for controlling movement of the first and second gripping surfaces between a gripping orientation in which the first and second gripping surfaces engage a guidewire positioned therebetween and a sliding orientation in which the first and second gripping surfaces are sufficiently spaced to permit free movement of a guidewire therebetween. The compression member includes first and second outwardly extending arms which respectively wrap about an exterior surface of the gripping member adjacent the first and second gripping surfaces to force the first and second gripping surfaces toward each other when the compression member is moved toward the gripping member.

15 Claims, 4 Drawing Sheets

GUIDE WIRE STEERING HANDLE

BACKGROUND OF THE INVENTION

1. Field of the Invention

The invention relates to guidewire steering devices. More particularly, the invention relates to side loading guidewire steering devices adapted for one-hand manipulation.

2. Description of the Prior Art

Interventional medical procedures involving guidewire introduction, insertion and manipulation are well known. For example, angioplasty generally includes the steps of inserting a guidewire through a vascular access needle into the femoral artery, and manipulating the external proximal end of the guidewire to advance the distal end of the guidewire through the patient's arterial tree to a predetermined vascular destination. A conventional dilatation, or other percutaneous catheter is then easily and rapidly fed over the guidewire directly into the vasculature to perform an appropriate diagnostic or therapeutic procedure. Similar guidewire applications are utilized in the introduction, removal and/or exchange of various catheters and like apparatus.

Insertion and manipulation of guidewires is often difficult and time consuming. Handling of guidewires is further complicated by the fact that conventional guidewires are generally provided with protective coatings that prevent blood from clotting on the guidewire, improve biocompatibility and enhance the guidewires maneuverability through the vascular system. However, such coatings often become more slippery when wetted, particularly with blood.

With this in mind, and in consideration of the size and material characteristics of conventional guidewires, it is extremely difficult to accurately and precisely handle and manipulate (e.g., pinch and torque) these small diameter guidewires with the fingers. As such, attempts have been made to provide guidewire steering devices which assist physicians and other medical practitioners in handling and maneuvering guidewires.

However, these prior art steering devices are replete with shortcomings which often frustrate physicians and limit procedure success. As such, a need exists for a user friendly guidewire steering device providing physicians with a convenient and reliable tool for handling guidewires. The present invention provides such a steering device.

SUMMARY OF THE INVENTION

It is an object of the present invention to provide a guidewire steering device. The device includes a gripping member having opposed first and second gripping surfaces positioned for selective engagement of a guidewire positioned therebetween. The first gripping surface includes a first end and a second end and the second gripping surface includes a first end and a second end, the first and second gripping surfaces being oriented to permit selective gripping of a guidewire positioned therebetween. The second end of the first gripping surface and the second end of the second gripping surface are spaced apart in a manner defining a lateral access slot through which a guidewire may be passed for positioning between the first and second gripping surfaces. A compression member is positioned about the gripping member for controlling movement of the first and second gripping surfaces between a gripping orientation in which the first and second gripping surfaces engage a guidewire positioned therebetween and a sliding orientation in which the first and second gripping surfaces are sufficiently spaced to permit free movement of a guidewire therebetween. The compression member includes first and second outwardly extending arms which respectively wrap about an exterior surface of the gripping member adjacent the first and second gripping surfaces to force the first and second gripping surfaces toward each other when the compression member is moved toward the gripping member.

It is also an object of the present invention to provide a guidewire steering device wherein the compression member includes a locking mechanism which selectively locks the gripping member in a gripping orientation.

It is another object of the present invention to provide a guidewire steering device wherein the locking mechanism includes a first locking element associated with the first outwardly extending arm and a second locking element associated with the second outwardly extending arm, the first locking element being shaped and dimensioned for frictionally engaging the exterior surface of the gripping member so as to lock the first outwardly extending arm relative to the gripping member and the second locking element being shaped and dimensioned for frictionally engaging the exterior surface of the gripping member so as to lock the second outwardly extending arm relative to the gripping member.

It is a further object of the present invention to provide a guidewire steering device wherein the first locking element is a projection shaped and dimensioned for receipt within a first recess formed along the exterior surface of the gripping member adjacent the first gripping surface and the second locking element is a projection shaped and dimensioned for receipt within a second recess formed along the exterior surface of the gripping member adjacent the second gripping surface.

It is also another object of the present invention to provide a guidewire steering device wherein the compression member includes a first end and a second end coupled by a resilient arm, the first end being rigidly secured to the gripping member such that the second end may be selectively moved toward the gripping member to effect movement of the first and second gripping surfaces to a gripping orientation. The first and second outwardly extending arms of the compression member are located adjacent the second end of the compression member.

It is still another object of the present invention to provide a guidewire steering device wherein a living hinge couples the first end of the first gripping surface to the first end of the second gripping surface.

It is yet another object of the present invention to provide a guidewire steering device wherein the gripping member is biased toward a sliding orientation with the first and second gripping surfaces sufficiently spaced to permit movement of a guidewire therebetween.

It is also an object of the present invention to provide a guidewire steering device wherein the gripping member is injection molded.

It is a further object of the present invention to provide a guidewire steering device wherein the gripping member is manufactured from a pliable material.

It is still a further object of the present invention to provide a guidewire steering device wherein the first end of the first gripping surface is coupled to the first end of the second gripping surface permitting controlled movement of the first and second gripping surfaces toward each so as to selectively grip a guidewire positioned therebetween.

It is also a further object of the present invention to provide a guidewire steering device wherein the first and second outwardly extending arms each include a camming surface which engages the exterior surface of the gripping member to force the first and second gripping surfaces toward each other when the compression member is moved toward the gripping member.

It is yet a further object of the present invention to provide a guidewire steering device wherein the lateral access slot is outwardly tapered to facilitate insertion of a guidewire therein.

It is also an object of the present invention to provide a guidewire steering device wherein the compression member is pivotally secured to the gripping member.

It is another object of the present invention to provide a guidewire steering device including a handle secured to the gripping member, the handle being separate and distinct from the compression member.

Other objects and advantages of the present invention will become apparent from the following detailed description when viewed in conjunction with the accompanying drawings, which set forth certain embodiments of the invention.

DESCRIPTION OF THE PREFERRED EMBODIMENT

Figure 1:
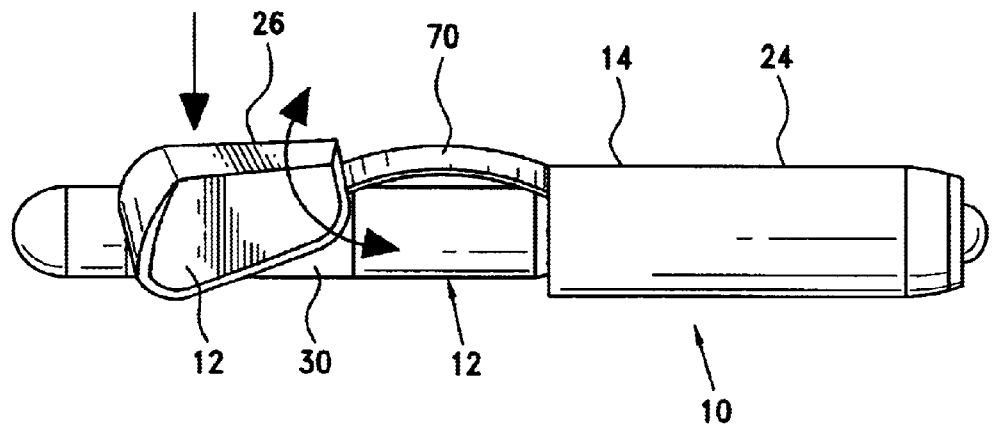
FIG. 1 is a side view of the steering handle with the compression member pressed downwardly to place the gripping member in a gripping orientation.
Figure 2:
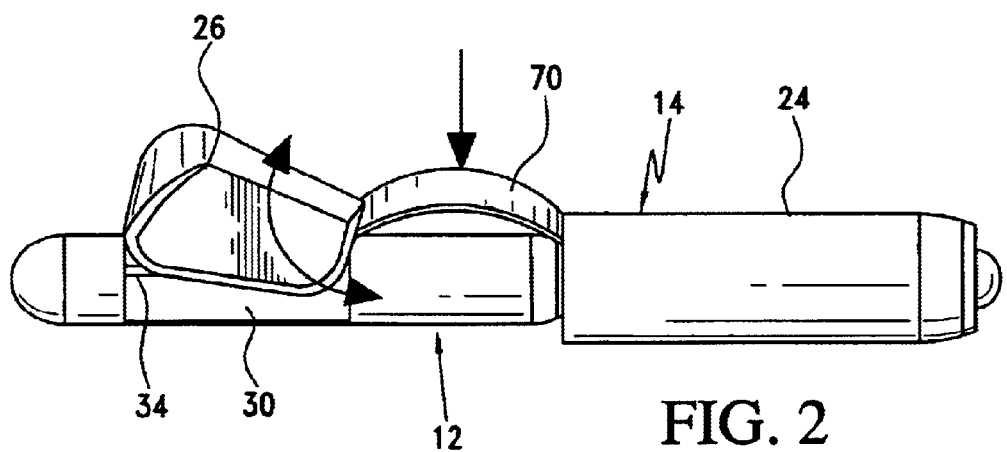
FIG. 2 is a side view of the steering handle with the compression member moved upwardly placing the gripping member in a sliding orientation.
Figure 3:
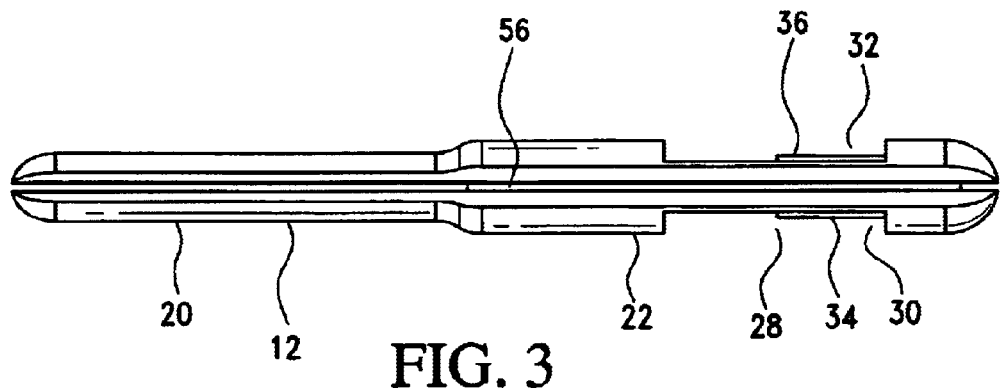
FIG. 3 is a top view of the gripping member showing the access slot.
Figure 4:
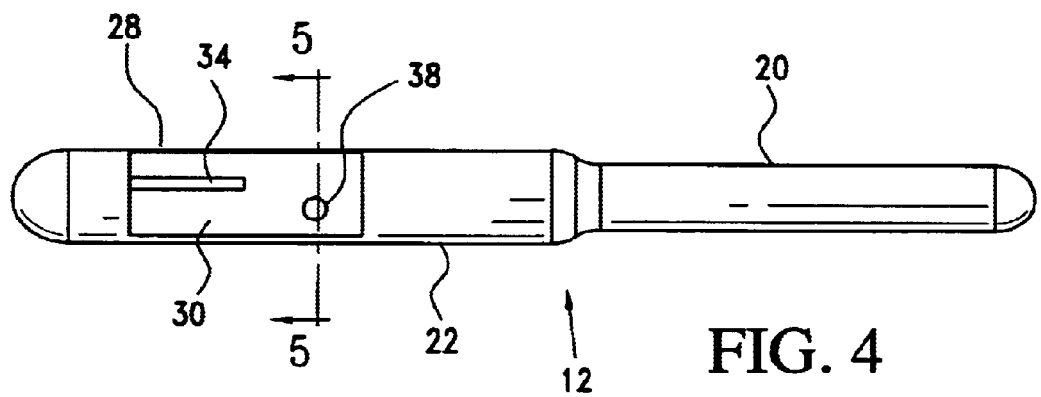
FIG. 4 is a side view of the gripping member.

The detailed embodiment of the present invention is disclosed herein. It should be understood, however, that the disclosed embodiment is merely exemplary of the invention, which may be embodied in various forms. Therefore, the details disclosed herein are not to be interpreted as limiting, but merely as the basis for the claims and as a basis for teaching one skilled in the art how to make and/or use the invention.

With reference to FIGS. 1 to 9, a guidewire steering device 10 in accordance with the present invention is disclosed. The guidewire steering device 10 generally includes a gripping member 12 and a compression member 14. In use, the compression member 14 straddles the flexing portion of the gripping member 12 to facilitate one handed loading and maneuvering of the present guidewire steering device 10. That is, the compression member 14 controls movement of the gripping member 12 between a gripping orientation in which first and second gripping surfaces 16, 18 engage a guidewire positioned therebetween and a sliding orientation in which first and second gripping surfaces 16, 18 are sufficiently spaced to permit free movement of a guidewire therebetween.

With reference to FIGS. 3 to 6, the gripping member 12 is formed with a one-piece construction. The gripping member 12 is preferably formed from PEBAX (polyether block amide) as it is stable under extended exposure to gamma radiation and/or ethylene oxide, and offers desirable flexing characteristics which will be better appreciated based upon the following disclosure. Although PEBAX is disclosed above as a preferred material, other pliable materials may be utilized without departing from the spirit of the present invention.

The gripping member 12 includes first and second ends 20, 22 having differing outer profiles. The first end 20 of the gripping member 12 is formed with a small diameter outer surface shaped and dimensioned for positioning a first end 24 of the compression member 14 thereabout. With regard to the second end 22 of the gripping member 12, it is generally circular in cross section, but includes a central portion 28 including opposed cut-outs 30, 32 shaped and dimensioned for placement and movement of a second end 26 of the compression member 14 thereabout. As will be better appreciated based upon the following disclosure, each of the cut-outs 30, 32 is further provided with a compression rail 34, 36 facilitating movement of the gripping member 12 to a gripping orientation as the compression member 14 is moved downwardly over the second end 22 of the gripping member 12. Each of the cut-outs 30, 32 is also provided with a recess 38, 40 shaped and dimensioned for receiving a locking element 42, 44 of the compression member 14 so as frictionally hold the compression member 14 relative to the gripping member 12.

Figure 5:
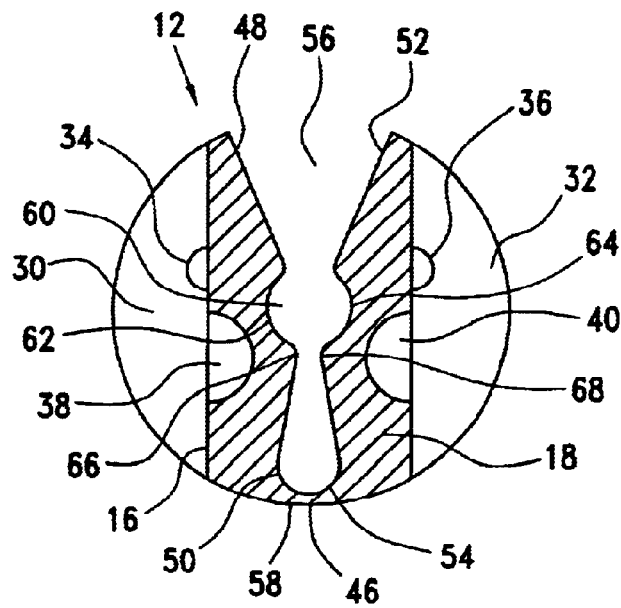
FIG. 5 is a cross sectional view of the gripping member along the line B—B.
Figure 6:
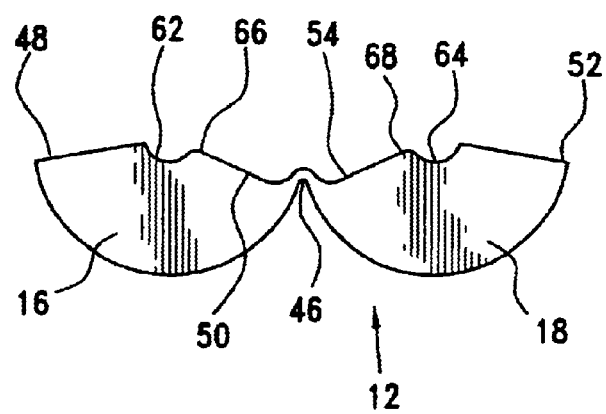
FIG. 6 is an end view of the gripping member.

As shown in FIGS. 5 and 6, the gripping member 12 has a generally C-shaped cross section and includes opposed first and second gripping surfaces 16, 18 positioned for selective engagement of a guidewire positioned therebetween. The first and second gripping surfaces 16, 18 are coupled by a connecting member 46 extending therebetween.

Specifically, the first gripping surface 16 includes a first end 48 and a second end 50 and the second gripping surface 18 includes a first end 52 and a second end 54. The second end 50 of the first gripping surface 16 and the second end 54 of the second gripping surface 18 are spaced apart in a manner defining a lateral access slot 56 through which a guidewire may be passed for positioning between the first and second gripping surfaces 16, 18. In fact, and as will be discussed in greater detail below, the lateral access slot 56 tapers outwardly as it extends toward the second ends 50, 54 of the respective first and second gripping surfaces 16, 18.

With regard to the other end of the gripping member 12, the first end 48 of the first gripping surface 16 is coupled to the first end 52 of the second gripping surface 18 permitting controlled movement of the first and second gripping surfaces 16, 18 toward each other so as to selectively grip a guidewire positioned therebetween. A living hinge 58 couples the first end 48 of the first gripping surface 16 to the first end 52 of the second gripping surface 18. The use of a living hinge 58 allows for the unitary manufacture of the gripping member 12 via injection molding. However, those skilled in the art will appreciate that multiple part constructions and other manufacturing techniques are possible within the spirit of the present invention.

Secure and convenient gripping of a guidewire positioned between the first and second gripping surfaces 16, 18 is facilitated by providing each of the first and second gripping surfaces 16, 18 with a profile well suited for use in the present application. Specifically, and as briefly discussed above, first and second gripping surfaces 16, 18 define an outwardly tapering access slot 56. The access slot 56 is provided for side loading of a guidewire within the present steering device 10. The large taper provided in accordance with a preferred embodiment of the present invention allows for manipulation and loading of the guidewire into the central cavity 60 of the gripping member 12.

At the interior edge of the access slot 56, each of the first and second gripping surfaces 16, 18 are provided with opposed concave recesses 62, 64 defining a central cavity 60 into which a guidewire is preferably positioned during gripping. The opposed concave recesses 62, 64 of the first and second gripping surfaces 16, 18 are shaped and dimensioned for receiving and gripping guidewires as small as 0.010 inches to those as large as 0.038 inches. In accordance with a preferred embodiment of the present invention, two devices will be produced, one for handling guidewires between approximately 0.010 inches and 0.018 inches and another for handling guidewires between approximately 0.022 inches and 0.038 inches (no one currently manufactures guidewires between 0.018 inches and 0.022 inches). While specific guidewire sizes are disclosed in accordance with a preferred embodiment of the present invention, those skilled in the art will appreciate that the recesses may be sized to accommodate a wide variety of guidewire sizes without departing from the spirit of the present invention.

The remote edge 66, 68 of each concave recess 62, 64 removed from the lateral access slot 56 is enlarged so as to prevent the guidewire from extending beyond the concave recesses 62, 64 and into contact with the living hinge 58. Specifically, the remote edges 66, 68 of the first and second gripping surfaces 16, 18 are sized so as to define a space therebetween which is too small for the passage of a guidewire therebetween. In use, and when a guidewire is being gripped in accordance with the present invention, the remote edges 66, 68 are drawn toward each other, and meet, to prevent passage of a guidewire therebetween.

The remote edges 66, 68 provide a further function in that they provide the resiliency forcing the gripping member 12 to an open position when force is either released from, or not being applied to, the gripping member 12.

Figure 7:
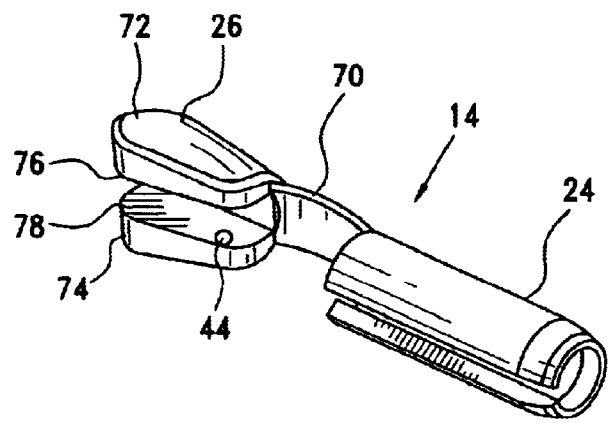
FIG. 7 is a perspective view of the compression member.
Figure 8:
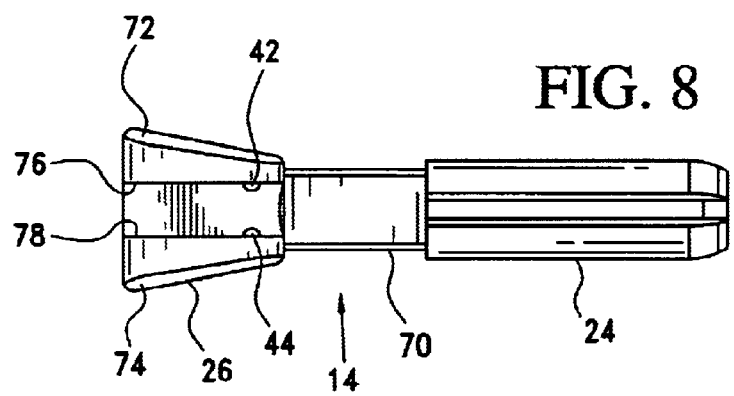
FIG. 8 is a bottom view of the compression member.
Figure 9:
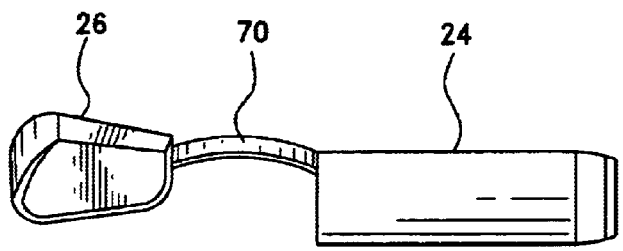
FIG. 9 is a side view of the compression member.
Figure 10:
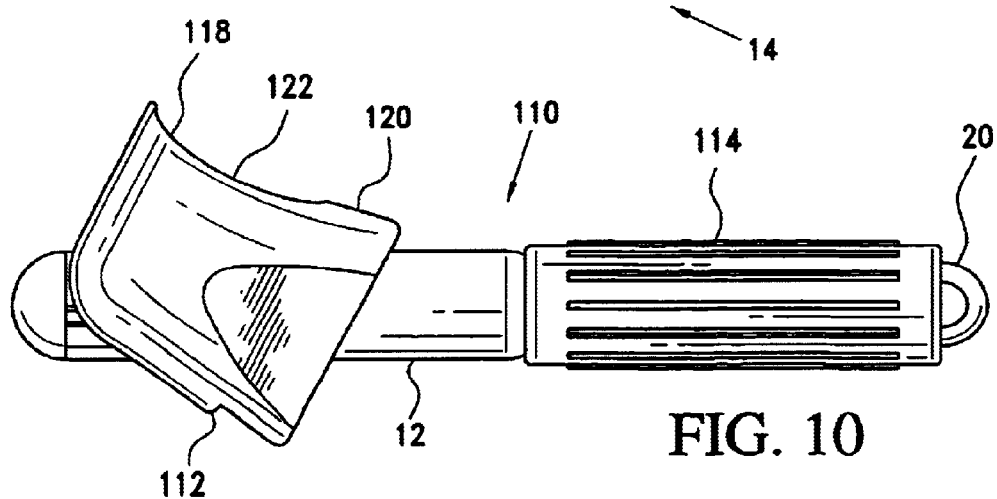
FIG. 10 is a side view of an alternate embodiment of the present invention.
Figure 11:
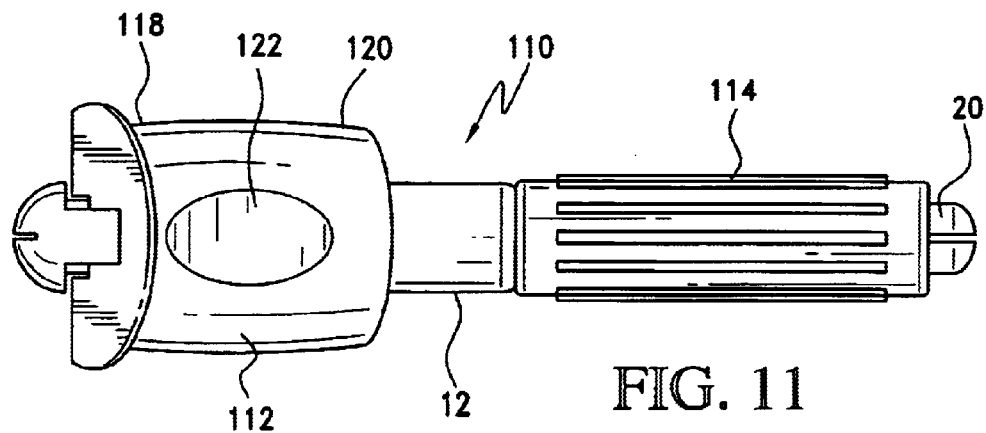
FIG. 11 is a top view of the embodiment disclosed in FIG. 10.
Figure 12:
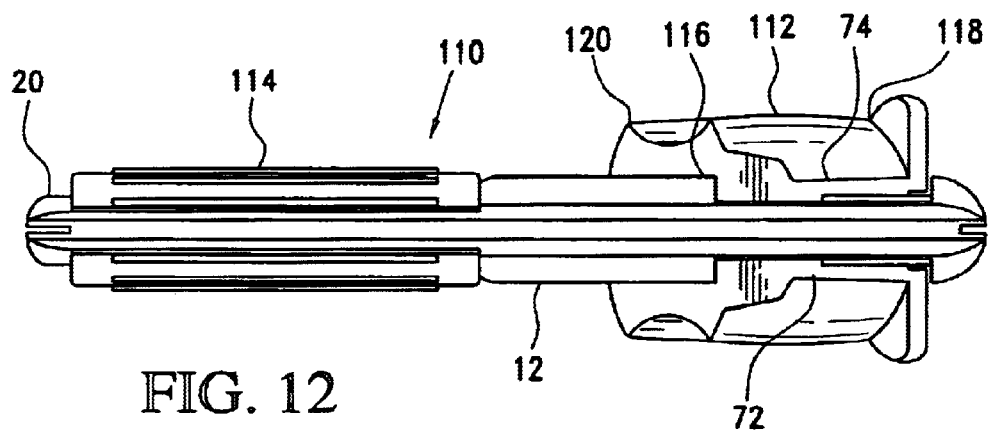
FIG. 12 is a bottom view of the embodiment disclosed in FIG. 10.
Figure 13:
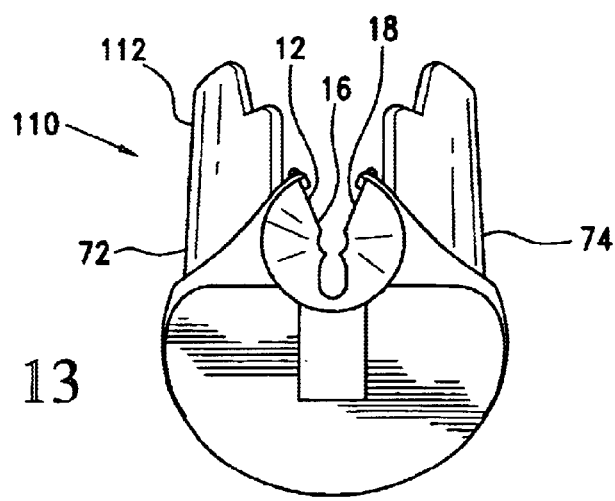
FIG. 13 is an end view of the embodiment disclosed in FIG. 10.

With regard to the compression member 14, and reference to FIGS. 7 to 9, the compression member 14 includes a first end 24 and a second end 26 coupled by a resilient arm 70. The first end 24 of the compression member 14 is rigidly secured to the first end 20 of the gripping member 12 such that the second end 26 maybe selectively moved toward the gripping member 12 to effect movement of the first and second gripping surfaces 16, 18 to a gripping orientation. With this in mind, the first end 24 of the compression member 14 acts as a base about which the second end 26 of the compression member 14 may be rotated when an operator simply applies downward pressure adjacent thereto.

With regard to the second end 26 of the compression member 14, it functions to impart movement to the first and second gripping surfaces 16, 18. This movement is accomplished by the provision of the first and second outwardly extending arms 72,74 which are shaped and dimensioned to fit within the cutouts 30, 32 formed along the second end 22 of the gripping member 12. The first and second arms 72, 74 respectively extend perpendicularly relative to the second end 26 of the compression member 14 so as to fit within the cut-outs 30, 32 along the second end 22 of the gripping member 12 and generally wrap about an exterior surface of the gripping member 12 adjacent the first and second gripping surfaces 16, 18 to force the first and second gripping surfaces 16, 18 toward each other when the compression member 14 is moved toward the gripping member 12.

The first and second outwardly extending arms 72,74 each include a camming surface 76,78 which engages the exterior surface of the gripping member 12, and particularly the compression rail 34, 36, to force the first and second gripping surfaces 16, 18 toward each other when the compression member 14 is moved toward the gripping member 12.

The compression member 14 further includes a locking mechanism which allows for selectively maintaining the gripping member 12 in a gripping orientation. The locking mechanism includes a first locking element 42 associated with the first outwardly extending arm 72 and a second locking element 44 associated with the second outwardly extending arm 74. The first locking element 42 is shaped and dimensioned for frictionally engaging the exterior surface of the gripping member 12 so as to lock the first outwardly extending arm 72 relative to the gripping member 12 and the second locking element 44 is shaped and dimensioned for frictionally engaging the exterior surface of the gripping member 12 so as to lock the second outwardly extending arm 74 relative to the gripping member 12. More specifically, the first locking element 42 is a projection shaped and dimensioned for receipt within a first recess 38 formed along the exterior surface of the gripping member 12 adjacent the first gripping surface 16 and the second locking element 44 is a projection shaped and dimensioned for receipt within a second recess 40 formed along the exterior surface of the gripping member 12 adjacent the second gripping surface 18.

In practice, as the second end 26 of the compression member 14 is forced downwardly, the first and second outwardly extending arms 72, 74 move downwardly over respective compression rails 34, 36. As the first and second outwardly extending arms 72, 74 then ride over the respective compression rails 34, 36 formed in each of the cut-outs 30, 32, they force the first and second gripping surfaces 16, 18 inwardly such that the first and second gripping surfaces 16, 18 contact a guidewire positioned therebetween. Further downward movement of the second end 26 of the compression member 14 causes the first and second locking elements 42, 44 to seat within the respective recesses 38, 40 formed within the cut-outs 30, 32, thereby "locking" the gripping member 12 in a gripping orientation. Release of the compression member 14 from this locked orientation is achieved by simply pressing downwardly on the resilient arm 70 connecting the first and second ends 24, 26 of the compression member 14. That is, the resilient arm 70 is shaped to cause movement of the second end 26 of the compression member 14 when downward pressure is applied thereto.

With reference to FIGS. 10 to 13, an alternate embodiment of the present steering device 110 is disclosed. The disclosed steering device 110 is substantially similar to the embodiment disclosed with reference to FIGS. 1 to 9, but includes separate first and second ends of the compression member. As such, like reference numerals will be used for those components which have not been changed.

Specifically, the embodiment disclosed in FIGS. 10 to 13 includes a compression member 112 and a handle 114. The handle 114 generally performs the functions of the first end 24 disclosed in accordance with the embodiment of FIGS. 1 to 9, while the compression member 112 generally performs the functions of the second end 26 disclosed in accordance with the embodiment of FIGS. 1 to 9. With this in mind, the handle 114 is rigidly secured to the first end 20 of the gripping member 12 and functions simply as a handle for gripping by a user of the present steering device 110.

With regard to the compression member 112, it functions just as the second end 26 to impart movement to the first and second gripping surfaces 16, 18. This movement is accomplished by the provision of the first and second outwardly extending arms 72, 74 which are shaped and dimensioned about the gripping member 12. The first and second arms 72, 74 generally wrap about an exterior surface of the gripping member 12 adjacent the first and second gripping surfaces 16, 18 to force the first and second gripping surfaces 16, 18 toward each other when the compression member 112 is moved toward the gripping member 12.

However, and in contrast to the second end 26 of the other embodiment, the compression member 112 is pivotally secured at a central position 116 thereof to the gripping member 12. As such, the compression member 112 includes a first end 118 which actually functions to compress the first and second gripping surfaces 16, 18 and a second end 120 which functions as a lever for pivoting the gripping member 12 between a gripping orientation and a sliding orientation. In practice, and beginning with the compression member 112 in its sliding orientation, a user need only place his or her finger upon the finger recess 122 and push downwardly and forwardly toward the first end 118 of the compression member 112, causing the compression member 112 to move downwardly forcing the first and second gripping surfaces 16, 18 into a gripping orientation. Release of the compression member 112 from this gripping orientation is achieved by simply pressing rearwardly and downwardly upon the recess 122 toward the second end 120 of the compression member 112, causing upward movement of the first end 118 of the compression member 112 which releases the first and second gripping surface 16, 18 to sliding orientation.

While the preferred embodiments have been shown and described, it will be understood that there is no intent to limit the invention by such disclosure, but rather, is intended to cover all modifications and alternate constructions falling within the spirit and scope of the invention as defined in the appended claims.

What is claimed is:

1. A guidewire steering device, comprising:
   a gripping member including opposed first and second gripping surfaces positioned for selective engagement of a guidewire positioned therebetween;
   the first gripping surface including a first end and a second end and the second gripping surface including a first end and a second end, the first and second gripping surfaces being oriented to permit selective gripping of a guidewire positioned therebetween;
   the first end of the first gripping surface and the first end of the second gripping surface being connected by a connecting member extending therebetween, and the second end of the first gripping surface and the second end of the second gripping surface being spaced apart in a manner defining a lateral access slot through which a guidewire may be passed for positioning between the first and second gripping surfaces;
   a compression member positioned about the gripping member for controlling movement of the first and second gripping surfaces between a gripping orientation in which the first and second gripping surfaces engage a guidewire positioned therebetween and a sliding orientation in which the first and second gripping surfaces are sufficiently spaced to permit free movement of a guidewire therebetween;
   the compression member including first and second outwardly extending arms which respectively wrap about an exterior surface of the gripping member adjacent the first and second gripping surfaces, each of the first and second outwardly extending arms include respective camming surfaces shaped and dimensioned to engage an outer surface of the gripping member to force the first and second gripping surfaces toward each other when the compression member is moved toward the gripping member.

2. The guidewire steering device according to claim 1, wherein the compression member includes a locking mechanism which selectively locks the gripping member in a gripping orientation.

3. The guidewire steering device according to claim 2, wherein the locking mechanism includes a first locking element associated with the first outwardly extending arm and a second locking element associated with the second outwardly extending arm, the first locking element being shaped and dimensioned for frictionally engaging the exterior surface of the gripping member so as to lock the first outwardly extending arm relative to the gripping member and the second locking element being shaped and dimensioned for frictionally engaging the exterior surface of the gripping member so as to lock the second outwardly extending arm relative to the gripping member.

4. The guidewire steering device according to claim 3, wherein the first locking element is a projection shaped and dimensioned for receipt within a first recess formed along the exterior surface of the gripping member adjacent the first gripping surface and the second locking element is a projection shaped and dimensioned for receipt within a second recess formed along the exterior surface of the gripping member adjacent the second gripping surface.

5. The guidewire steering device according to claim 1, wherein the compression member includes a first end and a second end coupled by a resilient arm, the first end being rigidly secured to the gripping member such that the second end may be selectively moved toward the gripping to effect movement of the first and second gripping surfaces to a gripping orientation; the first and second outwardly extending arms of the compression member being located adjacent the second end of the compression member.

6. The guidewire steering device according to claim 5, wherein the compression member includes a locking mechanism which selectively locks the gripping member in a gripping orientation.

7. The guidewire steering device according to claim 6, wherein the locking mechanism includes a first locking element associated with the first outwardly extending arm and a second locking element associated with the second outwardly extending arm, the first locking element being shaped and dimensioned for frictionally engaging the exterior surface of the gripping member so as to lock the first outwardly extending arm relative to the gripping member and the second locking element being shaped and dimensioned for frictionally engaging the exterior surface of the gripping member so as to lock the second outwardly extending arm relative to the gripping member.

8. The guidewire steering device according to claim 7, wherein the first locking element is a projection shaped and dimensioned for receipt within a first recess formed along the exterior surface of the gripping member adjacent the first gripping surface and the second locking element is a projection shaped and dimensioned for receipt within a second recess formed along the exterior surface of the gripping member adjacent the second gripping surface.

9. The guidewire steering device according to claim 1, wherein the connecting member is a living hinge which couples the first end of the first gripping surface to the first end of the second gripping surface.

10. The guidewire steering device according to claim 1, wherein the gripping member is biased toward a sliding orientation with the first and second gripping surfaces sufficiently spaced to permit movement of a guidewire therebetween.

11. The guidewire steering device according to claim 1, wherein the gripping member is injection molded.

12. The guidewire steering device according to claim 1, wherein the gripping member is manufactured from a pliable material.

13. The guidewire steering device according to claim 1, wherein the lateral access slot is outwardly tapered to facilitate insertion of a guidewire therein.

14. The guidewire steering device according to claim 1, wherein the compression member is pivotally secured to the gripping member.

15. The guidewire steering device according to claim 14, further including a handle secured to the gripping member, the handle being separate and distinct from the compression member.

* * * * *